US012295831B2

(12) United States Patent
Tai et al.

(10) Patent No.: US 12,295,831 B2
(45) Date of Patent: May 13, 2025

(54) LIQUID ACCOMMODATING INTRAOCULAR LENS WITH AN ASYMMETRIC CHAMBER

(71) Applicants: California Institute of Technology, Pasadena, CA (US); University of Southern California, Los Angeles, CA (US)

(72) Inventors: Yu-Chong Tai, Pasadena, CA (US); Mark S. Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 0 days.

(21) Appl. No.: 18/508,702

(22) Filed: Nov. 14, 2023

(65) Prior Publication Data
US 2025/0127611 A1  Apr. 24, 2025

Related U.S. Application Data

(60) Provisional application No. 63/545,255, filed on Oct. 23, 2023.

(51) Int. Cl.
*A61F 2/16* (2006.01)
(52) U.S. Cl.
CPC .... *A61F 2/1635* (2013.01); *A61F 2002/1683* (2013.01); *A61F 2002/169* (2015.04);
(Continued)

(58) Field of Classification Search
CPC ................ A61F 2002/1681; A61F 2002/1683
See application file for complete search history.

(56) References Cited

U.S. PATENT DOCUMENTS

| 4,578,063 A | 3/1986 | Inman et al. |
| 4,666,445 A | 5/1987 | Tillay |

(Continued)

FOREIGN PATENT DOCUMENTS

| CN | 105377189 | 3/2016 |
| EP | 3068343 | 9/2016 |

(Continued)

OTHER PUBLICATIONS

Alfonso et al., "Prospective visual evaluation of apodized diffractive intraocular lenses," J Cataract Refract Surg, 33:1235-43, 2007.
(Continued)

*Primary Examiner* — Melanie R Tyson
*Assistant Examiner* — Yasniary De La Caridad Morales
(74) *Attorney, Agent, or Firm* — Mark P. Mathison

(57) ABSTRACT

An accommodating intraocular lens (IOL) is formed from an anterior or posterior half molded as a chambered, polymer sack with a mouth opening smaller than its largest width that is mated to another half molded as a pliable bowl having a rim larger than the rest of the half. The resulting shell has a seam that is parallel to and does not cross or touch the equator such that the IOL is asymmetric between its front and back. A circular depression around the optical axis can be made in the anterior and/or posterior half such that a surrounding capsular bag seals against the rim of the depression, and an interior of the depression(s) does not touch the capsular bag.

20 Claims, 7 Drawing Sheets

(52) U.S. Cl.
CPC ............. *A61F 2002/16901* (2015.04); *A61F 2002/16902* (2015.04); *A61F 2230/0013* (2013.01); *A61F 2240/001* (2013.01); *A61F 2250/0003* (2013.01); *A61F 2250/0013* (2013.01)

(56) References Cited

U.S. PATENT DOCUMENTS

| | | | |
|---|---|---|---|
| 4,685,921 | A | 8/1987 | Peyman |
| 4,816,031 | A | 3/1989 | Pfoff |
| 4,822,360 | A | 4/1989 | Deacon |
| 4,888,016 | A | 12/1989 | Langerman |
| 4,995,880 | A | 2/1991 | Galib |
| 5,035,710 | A | 7/1991 | Nakada et al. |
| 5,091,121 | A | 2/1992 | Nakada et al. |
| 5,213,579 | A | 5/1993 | Yamada et al. |
| 6,358,279 | B1 | 3/2002 | Tahi et al. |
| 7,137,994 | B2 | 11/2006 | de Juan, Jr. et al. |
| 7,326,649 | B2 | 2/2008 | Rodger et al. |
| 7,569,048 | B2 | 8/2009 | Brown |
| 7,774,931 | B2 | 8/2010 | Tai et al. |
| 7,806,929 | B2 | 10/2010 | Brown |
| 7,883,540 | B2 | 2/2011 | Niwa et al. |
| 8,715,345 | B2 | 5/2014 | DeBoer et al. |
| 8,771,347 | B2 | 7/2014 | DeBoer et al. |
| 9,427,312 | B2 | 8/2016 | DeBoer et al. |
| 11,376,116 | B2 | 7/2022 | Webb |
| 2004/0068317 | A1 | 4/2004 | Knight |
| 2005/0177169 | A1 | 8/2005 | Fisher et al. |
| 2006/0047339 | A1 | 3/2006 | Brown |
| 2006/0084949 | A1 | 4/2006 | Peyman |
| 2006/0178741 | A1 | 8/2006 | Zadno-Azizi et al. |
| 2007/0004852 | A1 | 1/2007 | Mentak |
| 2007/0016294 | A1 | 1/2007 | Greenberg et al. |
| 2007/0213818 | A1 | 9/2007 | Carroazp |
| 2012/0303118 | A1 | 11/2012 | DeBoer et al. |
| 2012/0310343 | A1 | 12/2012 | Van Noy |
| 2013/0053954 | A1 | 2/2013 | Rao et al. |
| 2013/0150960 | A1 | 6/2013 | DeBoer et al. |
| 2013/0317608 | A1* | 11/2013 | Hermans ............... A61F 2/1624 623/6.34 |
| 2014/0180403 | A1 | 6/2014 | Silvestrini et al. |
| 2014/0330375 | A1* | 11/2014 | McCafferty ........... A61F 2/1635 623/6.34 |
| 2016/0184090 | A1 | 6/2016 | Shi et al. |
| 2018/0161151 | A1* | 6/2018 | Honigsbaum ......... A61F 2/1648 |
| 2019/0209291 | A1* | 7/2019 | Dudee .................. A61F 2/1694 |
| 2020/0008931 | A1 | 1/2020 | Argento et al. |
| 2022/0183820 | A1* | 6/2022 | Mueller ................... A61F 2/16 |
| 2022/0273423 | A1 | 9/2022 | Argento et al. |
| 2022/0387169 | A1 | 12/2022 | Ellis |

FOREIGN PATENT DOCUMENTS

| | | |
|---|---|---|
| JP | 61-122870 S | 6/1986 |
| JP | 63-200755 S | 8/1988 |
| JP | 04132547 | 5/1992 |
| JP | 04132547 A | 5/1992 |
| JP | 2004-022746 A | 8/1992 |
| JP | 11-505453 H | 5/1999 |
| JP | 2002-502666 A | 1/2002 |
| JP | 2002-516708 A | 6/2002 |
| JP | 2002-537066 A | 11/2002 |
| JP | 2003-532491 A | 11/2003 |
| JP | 2007089810 | 4/2007 |
| JP | 2008-520310 A | 6/2008 |
| JP | 2010-540070 A | 12/2010 |
| KR | 1020160086767 | 7/2016 |
| WO | 1999-40877 A1 | 8/1999 |
| WO | 2001-85067 A2 | 11/2001 |
| WO | 02/05015 A2 | 1/2002 |
| WO | 2005-050292 A1 | 6/2005 |
| WO | 2006/041550 A2 | 4/2006 |
| WO | 2006/074843 A1 | 7/2006 |
| WO | 2006/117208 A1 | 11/2006 |
| WO | 2009/021327 A1 | 2/2009 |
| WO | 2012-161749 A1 | 1/2012 |
| WO | 2015-073060 A1 | 5/2015 |

OTHER PUBLICATIONS

Atchison, D. et al., Optics of the Human Eye, p. 18, Oxford: Butterworth Heinemann. 2000.

Ben-Nun, J. et al., "Feasibility and development of a high-power real accommodating intraocular lens," J Cataract Refract Surg, 31:1802-08, 2005.

Burd, H. et al., "Numerical modeling of the accommodating lens," Vision Research, 42:2235-51, 2002.

Chong, L. et al., "A self-stabilizing lens ring for 25-gauge vitrectomy surgery," Am J Ophthalmol, 143:350-351, 2007.

Cillino, S. et al., "One-year outcomes with new-generation multifocal intraocular lenses," Ophthalmology, 115:1508-16, 2008.

Cumming, J. et al., "Clinical evaluation of the Crystalens AT-45 accommodating intraocular lens: Results of the U.S. Food and Drug Administration clinical trial," J Cataract Refract Surg, 32:812-825, 2006.

Duane, A., "Normal values of the accommodation at all ages," JAMA, 59(12):1020-13, 1912.

Dubbelman, M. et al., "Change in shape of the aging human crystalline lens with accommodation," Vision Res, 45:117-132, 2005.

Findl, O. et al., "Meta-analysis of accommodating intraocular lenses," J Cataract Refract Surg, 33:522-527, 2007.

Glasser, A. et al., "Presbyopia and the optical changes in the human crystalline lens with age," Vision Research, 38(2):209-229, 1998.

Glasser, A., "Restoration of accommodation: surgical options for correction of presbyopia," Clin Exp Optom, 91(3):279-295, 2008.

Hermans, E. et al., "Development of a ciliary muscle-driven accommodating intraocular lens," J Cataract Refract Surg, 34:2133-2138, 2008.

Heys, K. et al., "Massive increase in the stiffness of the human lens nucleus with age: the basis for presbyopia?" Mol Vis, 10:956-963, 2004.

Kasthurirangan, S. et al., "MRI study of the changes in crystalline lens shape with accommodation and aging in humans," J Vis, 11(3):19, 1-16, 2011.

Kessler, J., "Experiments in refilling the lens," Arch Ophthalmol, 71:412-417, 1964.

Koretz, J. et al., "Accommodation and presbyopia in the human eye—aging of the anterior segment," Vision Research, 29(12):1685-92, 1989.

Koopmans, S.A. et al., "Accommodative lens refilling in rhesus monkeys," Invest Ophthalmol Vis Sci, 47:2976-2984, 2006.

Koopmans, S.A. et al., "Polymer refilling of presbyopic human lenses in vitro restores the ability to undergo accommodative changes," Invest Ophthalmol Vis Sci, 44(1): 250-257, 2003.

Menapace, R. et al., "Accommodating intraocular lenses: a critical review of present and future concepts," Graefe's Arch Clin Exp Ophthalmol, 245:473-489, 2007.

Nishi, O. et al., "Accommodation amplitude after lens refilling with injectable silicone by sealing the capsule with a plug in primates," Arch Ophthalmol, 116:1358-61, 1998.

Nishi, O. et al., "Amplitudes of accommodation of primate lenses refilled with two types of inflatable endocapsular balloons," Arch Ophthalmol, 111:1677-1684, 1993.

Nishi, Y. et al., "Lens refilling to restore accommodation," J Cataract Refract Surg, 35:374-382, 2009.

Ossma, I. et al., "Synchrony dual-optic accommodating intraocular lens. Part 2: Pilot clinical evaluation," J Cataract Refract Surg, 33:47-52, 2007.

Pau, H., et al., "The increasing sclerosis of the human lens with age and its relevance to accommodation and presbyopia," Graefe's Arch Clin Exp Ophthalmol, 229:294-296, 1990.

Qiao, W. et al., "Bio-inspired accommodating fluidic intraocular lens," Opt Lett, 34(20):3214-16, 2009.

(56) References Cited

OTHER PUBLICATIONS

Rosales, P. et al., "Crystalline lens radii of curvature from Purkinje and Scheimpflug imaging," J Vis, 6:1057-67, 2006.
Strenk, S. et al., "Age-related changes in human ciliary muscle and lens: Magnetic resonance imaging study," Invest Ophthalmol Vis Sci, 40:1162-69, 1999.
Strenk, L. et al., "The mechanism of presbyopia," Progress in Retinal and Eye Research, 24:379-393, 2005.
Von Helmholtz, H., "§12. Mechanism of Accommodation," Helmholtz's Treatise on Physiological Optics, pp. 143-172, Optical Society of America, 1924.
Weeber, H.A. et al., "Stiffness gradient in the crystalline lens," Graefe's Arch Clin Exp Ophthalmol, 245:1357-66, 2007.
Wolffsohn, J. el al., "Subjective and objective performance of the Lenstec KH-3500 "accommodative" intraocular lens," Br J Ophthalmol, 90:693-696, 2006.
Zhao, G. et al., "Visual function after monocular implantation of apodized diffractive multifocal or single-piece monofocal intraocular lens: Randomized prospective comparison," J Cataract Refract Surg, 36(9):282-285, 2010.
Fisher, "The Force of Contraction of the Human Ciliary Muscle During Accommodation," J. Physiol., 1977, vol. 270, pp. 51-74.
Fisher, "The Significance of the Shape of the Lens and Capsular Energy Changes in Accommodation," J. Physiol., 1969, vol. 201, pp. 21-47.
Fisher, "Some Experimental Studies of Human Accommodation and Presbyopia," (Summary) Recent Advances in Visual Sciences, Section of Ophthalmology, Oct. 1973, vol. 66, p. 1037.
Floyd et al., "Capsular bag opacification with a new accommodating intraocular lens," J Cataract Refract Surg, 2013, vol. 39, pp. 1415-1420.
Glasser et al., "Aging of the Human Crystalline Lens and Presbyopia," International Ophtalmology Clinics, Spring 2001, vol. 41, Issue 2, pp. 1-15.
Glasser et al., "Biometric, optical and physical changes in the isolated human crystalline lens with age in relation to presbyopia," Vision Research, 1999, vol. 39, pp. 1991-2015.
Koeppl et al., "Pilocarpine-induced shift of an accommodating intraocular lens: AT-45 Crystalens," J Cataract Refract Surg, 2005, vol. 31, pp. 1290-1297.
Leishman et al., "Prevention of capsular bag opacification with a modified hydrophilic acrylic disk-shaped intraocular lens," J Cataract Refract Surg, 2012, vol. 38, pp. 1664-1670.
Souza et al., "Visual Performance of AcrySof ReSTOR Apodized Diffractive IOL: A Prospective Comparative Trial," Am J Ophthalmol., 2006, vol. 141, pp. 827-832.
Werner et al., "Capsular bag opacification after experimental implantation of a new accommodating intraocular lens in rabbit eyes," J Cataract Refract Surg, 2004, pp. 111-1123.

\* cited by examiner

LIQUID ACCOMMODATING INTRAOCULAR LENS WITH AN ASYMMETRIC CHAMBER

CROSS-REFERENCES TO RELATED APPLICATIONS

This application claims the benefit of U.S. Provisional Application No. 63/545,255, filed Oct. 23, 2023, which is hereby incorporated by reference in its entirety for all purposes.

STATEMENT AS TO RIGHTS TO INVENTIONS MADE UNDER FEDERALLY SPONSORED RESEARCH AND DEVELOPMENT

Not applicable.

BACKGROUND

1. Field of the Art

The present disclosure relates to the technical field of intraocular lens prostheses implantable into the body, and more particularly, to a liquid accommodating intraocular lens having an adjustable focus by way of changing shape facilitated by a differently shaped anterior half than its posterior half. Either the anterior or posterior lens half is molded as a wide-mouth sack where the mouth is smaller than the widest circumference, the other half is molded like a pliable bowl, and the two halves are joined such that the seam is clear of the widest circumference.

2. Description of the Related Art

Cataract extraction combined with intraocular lens (IOL) implantation remains one of the only effective treatments for cataracts now and for some time to come. Although the implantation of a traditional monofocal intraocular lens after cataract surgery can obtain good distance vision, a monofocal intraocular lens does not have the ability to adjust focus. Patients generally have farsightedness after surgery and need to rely on glasses to meet the requirements of different close-range work.

Multifocal intraocular lens adopts a unique optical design that can simultaneously form two or more focal points in the eye. After surgery, patients can adjust the pupil size and choose different focal points to meet the needs of farsightedness and near-sightedness, which reduces the rate of wearing glasses after surgery for cataract patients. But when there are multiple focal points, they will produce halos, glare and other shortcomings for patients.

In recent years, some scholars have tried to design adjustable intraocular lenses by changing the filling amount of the optical fluid medium (e.g., silicone oil) in the capsular bag or changing the type of optical fluid medium.

There is a need in the art for improved intraocular lenses that can be adjusted, preferably, by a patient's own ciliary eye muscles.

BRIEF SUMMARY

Generally described is a liquid-inflatable intraocular lens having an anterior or posterior half molded as a wide-mouth flexible sack whose opening slightly curves in to form a mouth that is slightly smaller than the sack's widest portion. The widest portion is sometimes referred to as an equator. The sack is joined to another half that is molded as more of a slightly gumdrop-shaped, pliable bowl whose widest portion is at its opening. The two halves are joined together to form a watertight pliable shell whose seam is neither on nor crosses its equator. The shell, which is inflatable through a self-sealing valve, is considered "asymmetric" between its anterior (front) and posterior (rear) portions.

A depression can be molded on one or both the anterior and posterior halves such that, when inflated to fill a patient's capsular bag, the capsular bag forms a taut seal all of the way around the rim of the depression. That is, the depression's rim is continuous without peaks, notches, or other features that would interfere with the seal. The depression can be deep enough that its highest portion, which is usually in the center, does not touch the capsular bag overhead.

Haptic arms can project out from the equator or from areas flanking, but not on, the equator. Pairs of haptic arms that flank the equator or seam can be joined at their ends.

Some embodiments of the invention are related to a first half formed from a polymer sack having a mouth smaller than an equator of the sack, a second half formed from a pliable bowl with a rim, a seam joining the mouth of the first half with the rim of the second half to form a liquid-inflatable shell, an optical axis passing through the first half and the second half, and a sealable valve in the shell.

The seam can be parallel to the equator. A distance between the seam and the equator can be between 1.0 millimeter and 1.5 millimeters.

A depression can be formed in the shell, the depression having a continuous rim disposed around the optical axis, the continuous rim configured to seal against an enveloping capsular bag when implanted. A highest point within the depression can be lower than the continuous rim when the shell is full of liquid, the depression being configured to hold an enveloping capsular bag away from shell wall material within the depression. A second depression can be formed in the shell as well, on the opposing hemisphere, the second depression having a continuous rim disposed around the optical axis, the continuous rim of the second depression configured to seal against an enveloping capsular bag when implanted. A highest point within the second depression can be lower than the continuous rim of the second depression when the shell is full of liquid, the second depression being configured to hold an enveloping capsular bag away from shell wall material within the second depression.

A haptic can be connected to the equator. A first set of haptic arms can project from areas on the shell that are not on the equator. A second set of haptic arms can project from areas on the shell on an opposite hemisphere of the equator from the first set of haptic arms. Ends of the first and second haptic arms can be joined together. The first set of haptic arms can be connected to the first half at one-half the thickness of the first shell half, and the second set of haptic arms can be connected to the second half at one-half the thickness of the second shell half.

The sealable valve can include an annulus and a self-sealing polymer body surrounded by the annulus, the polymer body being softer than the annulus. A hardness of the annulus can be between 80A Shore and 90A Shore, and a hardness of the polymer body is between 20A Shore and 40A Shore. A layer of parylene can be laid over the sealable valve. Liquid can fill the liquid-inflatable shell.

Some embodiments are related to a method of manufacturing and testing an accommodating intraocular lens, the method including providing a first half formed from a polymer sack having a mouth smaller than an equator of the sack, providing a second half formed from a pliable bowl with a rim, joining the mouth of the first half with the rim of the second half to form a liquid-inflatable shell, an optical axis passing through the first half and the second half, and filling, through a sealable valve, the shell with liquid.

The joining can include adding uncured polymer across the first and second halves to form a seam, wherein the seam is parallel to the equator. During testing or otherwise, one can squeeze or pull the equator, and such squeezing or pulling can increase a wall curvature of the one of the halves around the optical axis more than a wall curvature of the other half around the optical axis. The method can further include joining an end of a first haptic arm projecting from a point on the shell not on the equator to an end of a second haptic arm projecting from a point on the shell on an opposite hemisphere of the equator from the first haptic arm

DETAILED DESCRIPTION

A liquid-fillable accommodating intraocular lens (IOL) is described with different anterior and posterior halves. One of the halves is cavitied or chambered in that its opening, or mouth, is smaller than its widest section within. The other half is more of an open bag whose mouth is at its widest point. When the two halves are welded or otherwise joined together, a seam between the two halves does not fall on the resulting shell's largest circumference, otherwise known as the equator.

Thus, the anterior and posterior halves or capsules in the accommodating intraocular lens are asymmetric with respect to each other. The design avoids having their the seam at the equator, advantageously reducing the stress concentration or deformation of the entire capsule shell, and obtaining good mechanical properties, which can improve the refractive effect of the intraocular lens.

One or more sealable valves, or designated areas for needles to pass through, are provided on the anterior face of the IOL so that a physician may fill the shell after implantation into a patient's eye, typically into the capsular bag.

"Bisect" includes dividing into two sections, or as otherwise known in the art. The two sections are not necessarily equal parts.

A "circumference" of a 3-dimensional object includes a circumference of a circle, oval, or other closed-form shape around a central axis as seen from a cross-section view of the object, or as otherwise known in the art. It does not necessarily mean the largest circumference of the object.

An "equator" of a 3-dimensional object includes a largest circumference of an object, or as otherwise known in the art.

A "half" or "hemisphere" of a device is a portion of the device when it is divided into or comes from two parts, or as otherwise known in the art. A half is not necessarily anywhere near an exact half of an object but rather is a substantial portion of the device.

A "optical axis" of a device is a transparent area through which visible light is intended to pass, often but not required to define radial symmetry of the device therearound, or as otherwise known in the art.

A "sealable valve" includes an area designated for a needle to pass through and, by its material thickness, resilience, or other properties can automatically or otherwise seal when the needle is withdrawn, or as otherwise known in the art.

Figure 1:
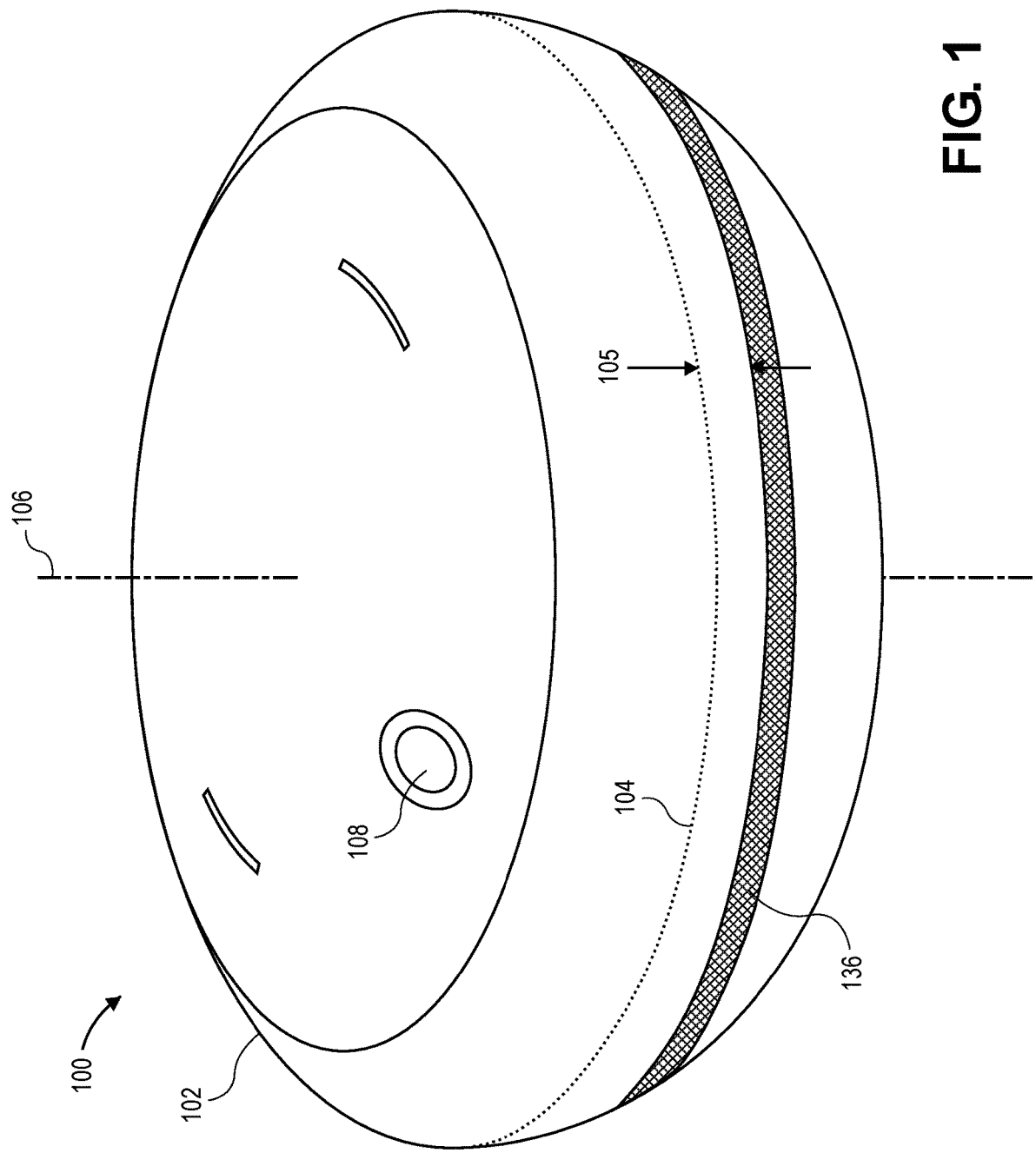
FIG. 1 is a perspective view of an accommodating intraocular lens device in accordance with an embodiment.

FIG. 1 is a perspective view of an accommodating intraocular lens device 100. It is composed of liquid-inflatable shell 102, which is made of a pliable polymer such a silicone, and as shown is fully inflated with liquid silicone. The shell, or capsule, is circular around optical axis 106 and has equator 104 defined by the farthest outer circumference from the optical axis.

The shell may be made of silica gel, siloxane, fluorosilane, or hydrophilic or hydrophobic acrylate. In some cases, silica gel is preferred.

The anterior capsule (shown at the top in the figure) and the posterior capsule (shown at the bottom in the drawing) can be bonded whole to form a near-ellipsoid structure that mimics the human lens. Solid glass lenses are sometimes plano-convex. The capsule shell is considered an asymmetric ellipsoidal shape. Where a radial (distance) line continues to increase from the front to the back, when the maximum value is reached, it begins to decrease if going backward, and the middle maximum value is at the equator. Because the equator is prone to stress concentrations or slight deformations, which affects the refractive effect, the seam of the anterior capsule and the posterior capsule should avoid the equator, so as to avoid the deformation of the capsule. Thus, the intended refractive effect can be better assured.

Seam 136 is formed between the anterior and posterior halves. Seam 136 is parallel to equator 104 with a constant distance of 105. It has been found that distances between 1.0 and 1.5 millimeters (mm) works well in some embodiments. Where the connection of the anterior capsule and the posterior capsule in the capsule form seam line 136, seam line 136 forms an integral ring. Thus, the seam line is subjected to a relatively uniform force when implanted.

Sealable valve 108, sometimes referred to as a sealing valve, is disposed on the mostly visible anterior half of the device. This affords access by an ophthalmologist to fill or adjust.

Figure 2A:
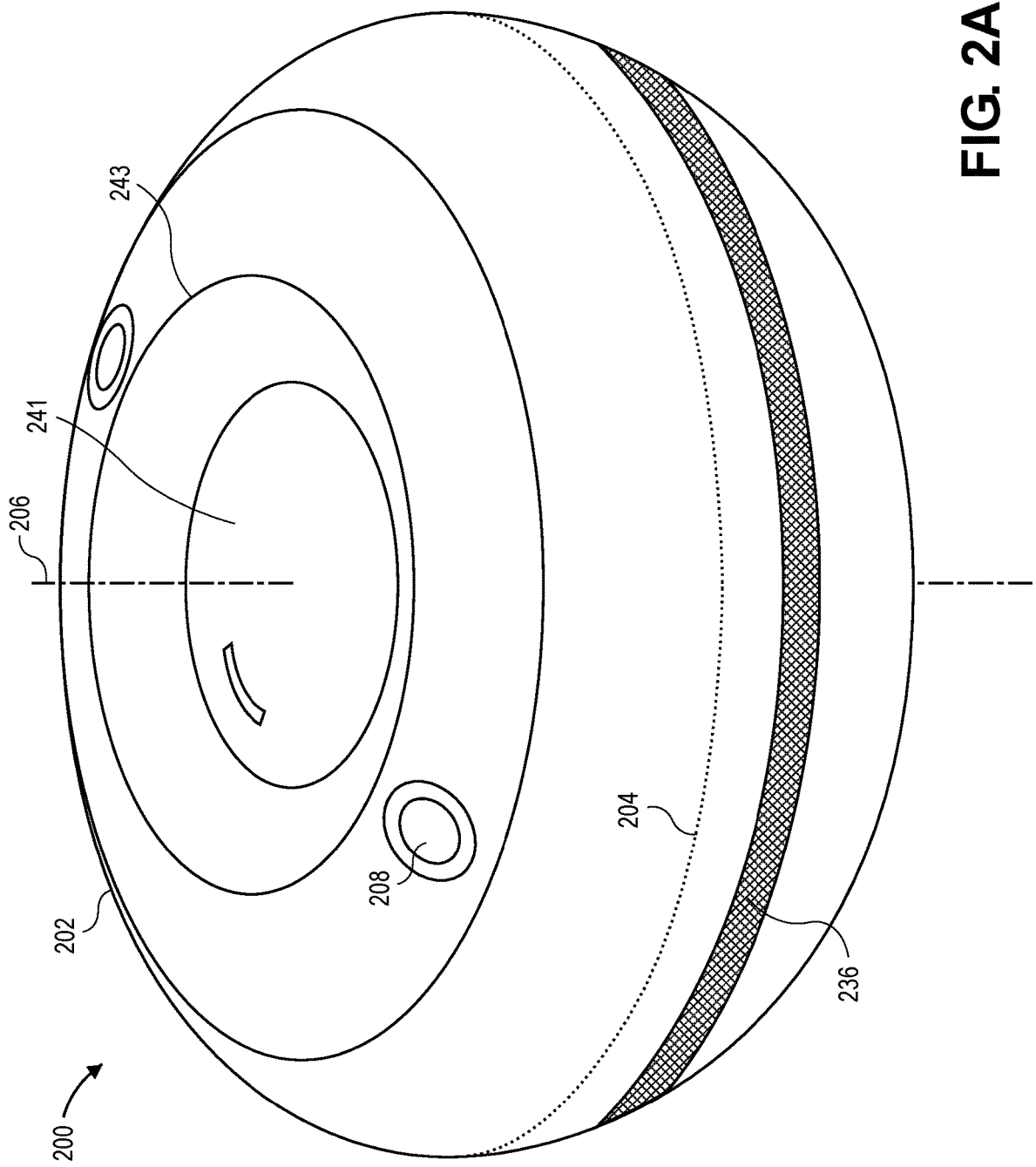
FIG. 2A is a perspective view of an accommodating intraocular lens device with a depression in accordance with an embodiment.
Figure 2B:
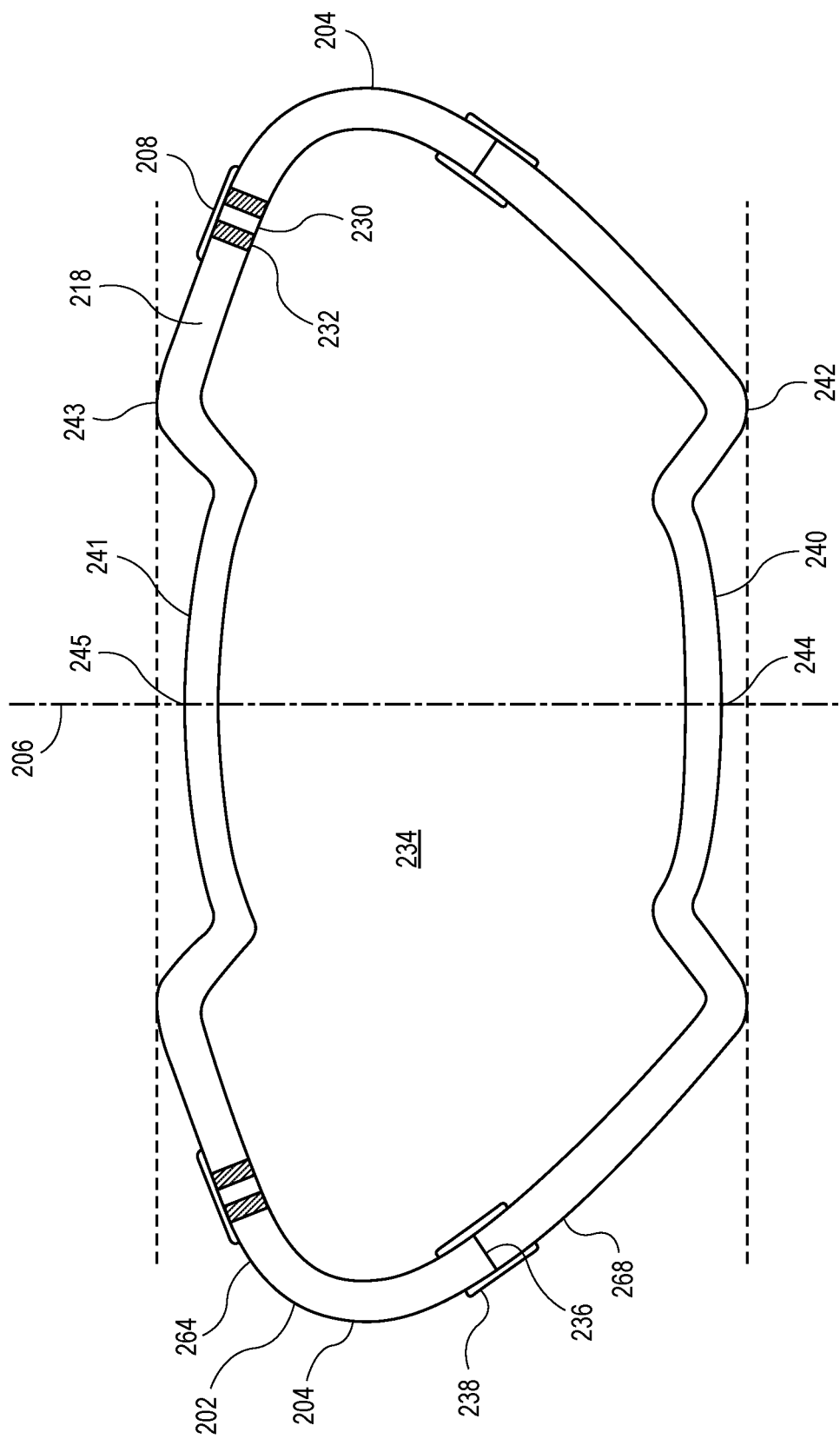
FIG. 2B is an axial cross section view of the intraocular lens device of FIG. 2A.

FIGS. 2A-2B illustrate an accommodating intraocular lens device 200. From FIG. 2A is evident a large feature in the anterior of shell 202: a sunken, recessed area.

As visible from the cross section in FIG. 2B, there are two such depressions, anterior depression 241 in anterior half 264 and posterior depression 240 in posterior half 268. Both anterior depression 241 and posterior depression 240 have continuous rims 243 and 242, respectively, surrounding them and optical axis 206. The continuous rims avoid having localized notches, sharp bumps, or other features so that the rims can seal against an enveloping capsular bag when shell 202 is implanted within a subject.

A technical advantage of the seal is that it helps prevent allogeneic tissue proliferation, wherein cells grow and migrate over time along the shell from outer regions to the middle where they can occlude vision around the optical axis.

Continuous rim 243 is higher than highest point 245 within depression 241 as shown in the figure. That is, any line from rim to rim does not touch any portion of the depression within the rim. Similarly, continuous rim 242 is higher (i.e., farther away from the inside) than highest point 244 within depression 240. This configuration holds enveloping capsular bag tissue away from wall 218 of shell 202.

A technical advantage of holding the wall away from the capsular bag is so that a surgical laser may be used to delicately cut a portion of the capsular bag without the laser beam's localized heat on the capsular bag melting the side of the shell.

During manufacture, shell 202 was combined from two halves, anterior half 264 and posterior half 268. The halves are joined at seam 236. Seam 236 runs all of the way around shell 202 but is neither disposed at nor crosses equator 204. Further, polymer 238 that was added to seal and helps reinforce the seam, now cured, neither is disposed at nor crosses equator 204.

A technical advantage of avoiding the equator with the seam, which often is thicker or less uniform in thickness than the rest of the shell, allows the equator to more consistently carry and transfer stresses that move the lenses with respect to each other.

Wall 218 of shell 202 wraps around the entire device. Outer circumferences of the wall are outside of the device, the largest labeled as device equator 204. Meanwhile, inner circumferences are on the inside of wall 218 facing optical filling liquid 234.

Optical filling mediums can include silicone oil, silicomethane, sterile heavy water for ophthalmology (perfluorodecalin C10F18), HEALON GV® sodium hyaluronate, and others.

Optical filling liquid 234 was injected through sealable valve 208. Sealable valve 208 includes hard-polymer annulus 232, sometimes referred to as a ring body, disposed within anterior half 264. Annulus 232 surrounds self-sealing polymer body 230, the Shore hardness of body 230 being less than that of annulus 232. For example, the hardness of the annulus can be between 80A-90A Shore, and the hardness of the polymer body is between 20A-40A Shore.

The valve body is preferably round and the annulus is preferably a ring. When injecting optical fluid medium from the sealable valve 208, due to the smaller hardness of body than the surrounding annulus it is locally suitable for the injection needle to enter capsule shell 202. Also with the soft body, it is easier to achieve sealing after the injection needle is withdrawn to prevent the leakage of the optical fluid medium. The annulus can be made of hard silicone, and the valve body made of soft silicone.

A parylene layer can cover the outer surface of the sealable valve 208 and also partially overlap the outer surface of the capsule 202. This overlap increases the contact area of the parylene layer and sealable valve 208 for adhesion and helps avoid a potential concentration of stress at the interface of sealable valve 208 and shell capsule 202.

The Young's modulus and hardness of the parylene layer are significantly higher than sealable valve 208, and the adhesion between the parylene layer and sealable valve 208 is better, which is equivalent to making a layer of reinforced baffle outside the sealing valve. Therefore, when an injection needle is withdrawn, the optical fluid medium (such as silicone oil) in the sealing valve can generate outward pressure on the sealing valve, and the outward pressure can make the sealing valve self-close under the protection of the rigid parylene layer, so that it can play a role in sealing and leakage prevention for a long term.

On the exemplary embodiment in the figure, there are two sealable valves 208 symmetrically disposed on the central axis 206 of the capsule 202. One of the sealable valves can be used for injection, and the other sealable valve may play a role in mechanical compensation and balancing, and can also be used as a spare valve. Other numbers of sealable valves may be used.

When the shell is full of liquid, radially pulling or pushing on the equator alters the curvature of wall 218. In some embodiments, the forces alter the wall curvature of the anterior half around the optical axis more than a wall curvature of the posterior half around the optical axis. This allows for asymmetric curvatures of the anterior and posterior optical areas.

A wall thickness of the anterior half can be thinner than a wall thickness of the posterior half, or vice versa, in order to facilitate preferred bending and curvatures.

Figure 3:
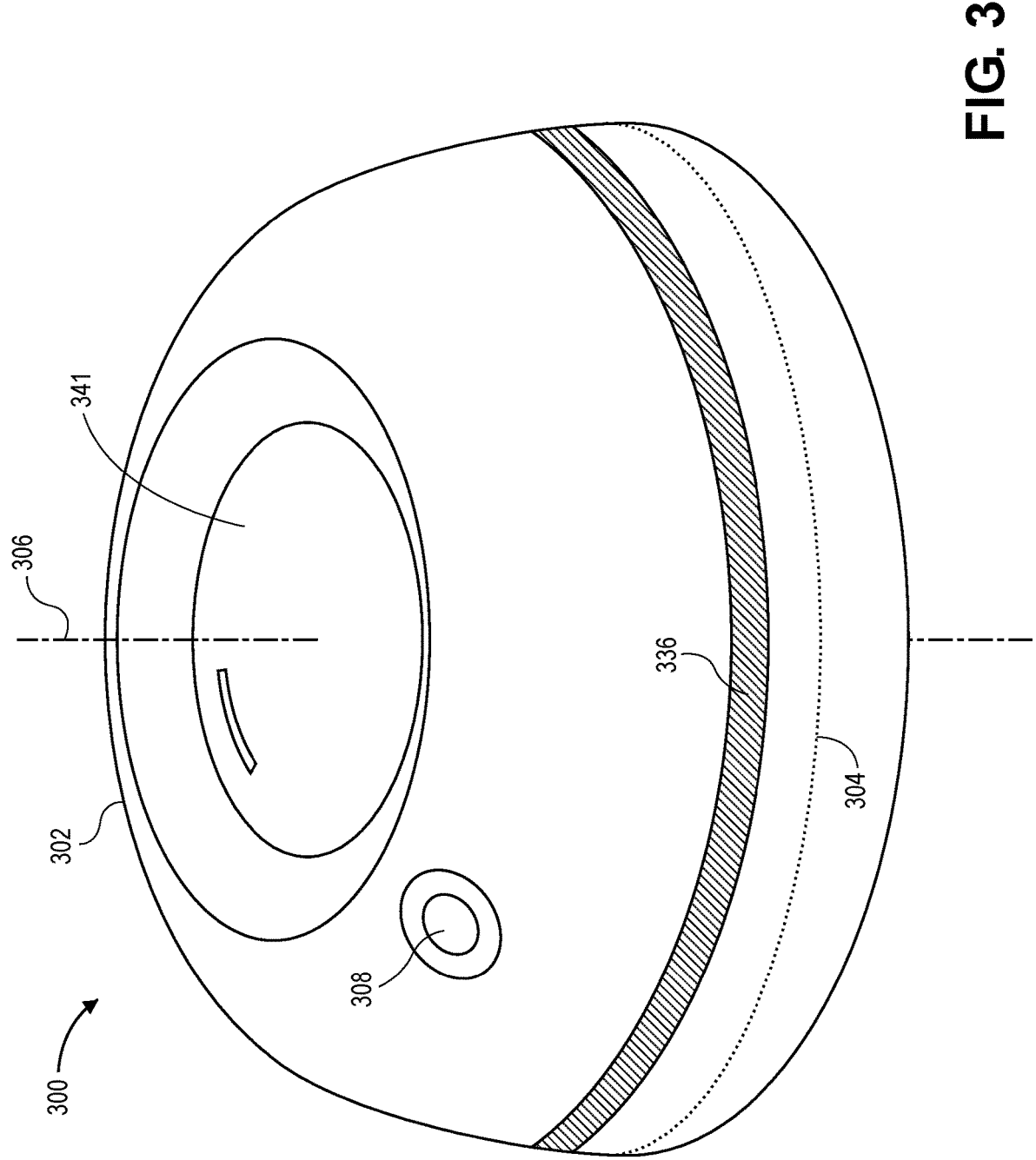
FIG. 3 is a perspective view of an accommodating intraocular lens device with a seam above an equator, when looking down at the anterior side, in accordance with an embodiment.

FIG. 3 is a perspective view of accommodating intraocular lens device 300 with a seam above an equator. That is, the anterior half was molded as a pliable bowl with a rim, and the anterior half was molded as a polymer sack having a mouth smaller than equator 304 of the sack.

The two halves were joined at the mouth of the first half with the rim of the second half to form liquid-inflatable shell 302, optical path 306 passing through both the anterior and posterior halves. The result is a shell that is more rounded on the anterior hemisphere than the posterior hemisphere, as shown in the figure.

Integral with the anterior hemisphere is sealable valve 308 and depression 341, the latter being symmetric around optical axis 306.

Figure 4:
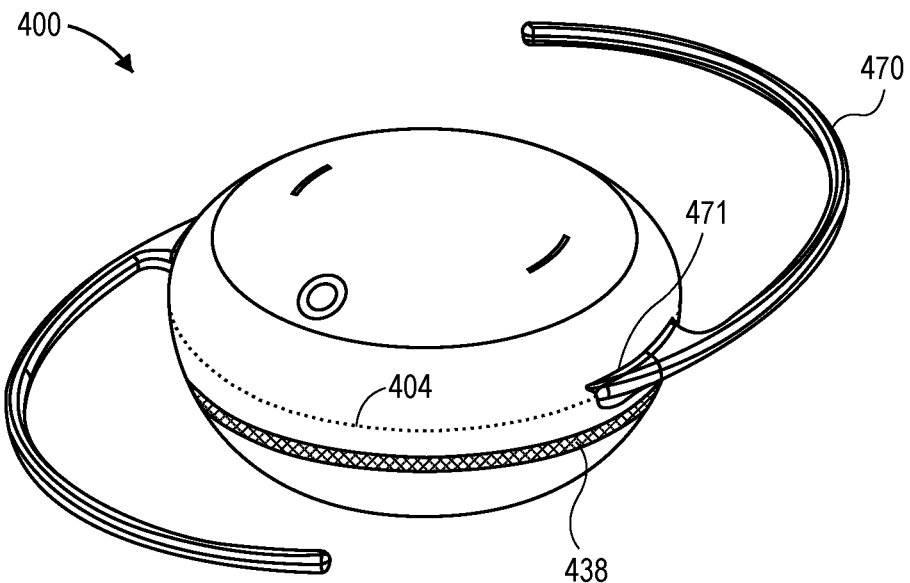
FIG. 4 is a perspective view of an accommodating intraocular lens device with haptics in accordance with an embodiment.
Figure 5:
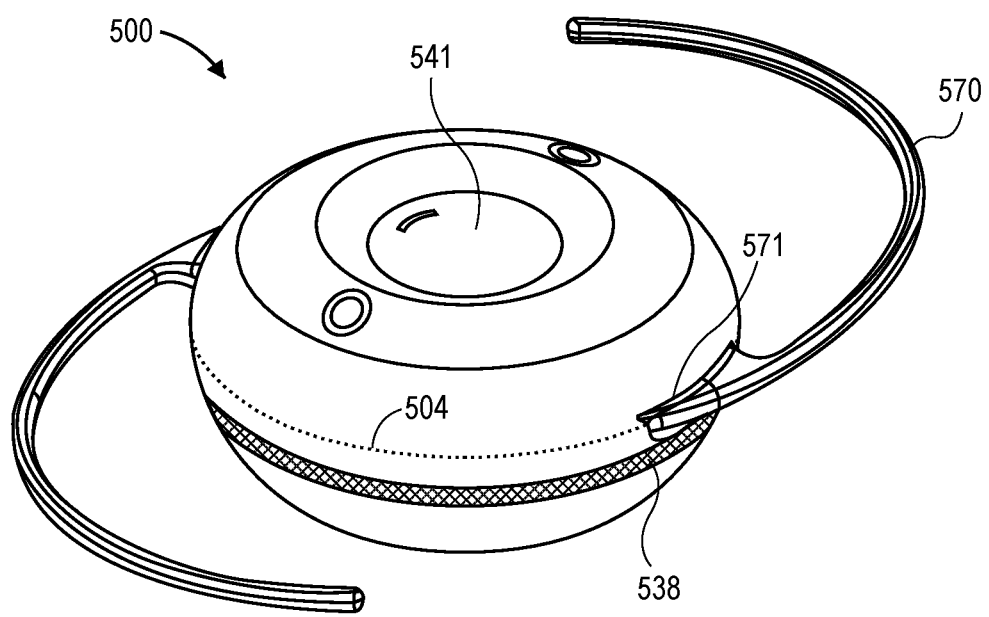
FIG. 5 is a perspective view of an accommodating intraocular lens device with haptics and a depression in accordance with an embodiment.

FIGS. 4 and 5 illustrate accommodating intraocular lens devices 400 and 500, respectively, with haptics.

In FIG. 4, haptic 470 projects outward from point 471. Point 471 is on equator 404, which avoids thickened polymer 438 around the seam.

In some embodiments, the anterior half lacks a depression but the posterior includes a groove or other depression. The bottom of the depression may be constructed as an optical lens. Converging or diverging lenses may be employed.

In FIG. 5, haptic 570 projects outward from point 571. Point 571 is on equator 504, not touching or crossing thickened polymer 538 around the seam. The figure also illustrates depression 541 in the anterior half. The bottom of the depression may be constructed as an optical lens, converging or diverging.

Figure 6A:
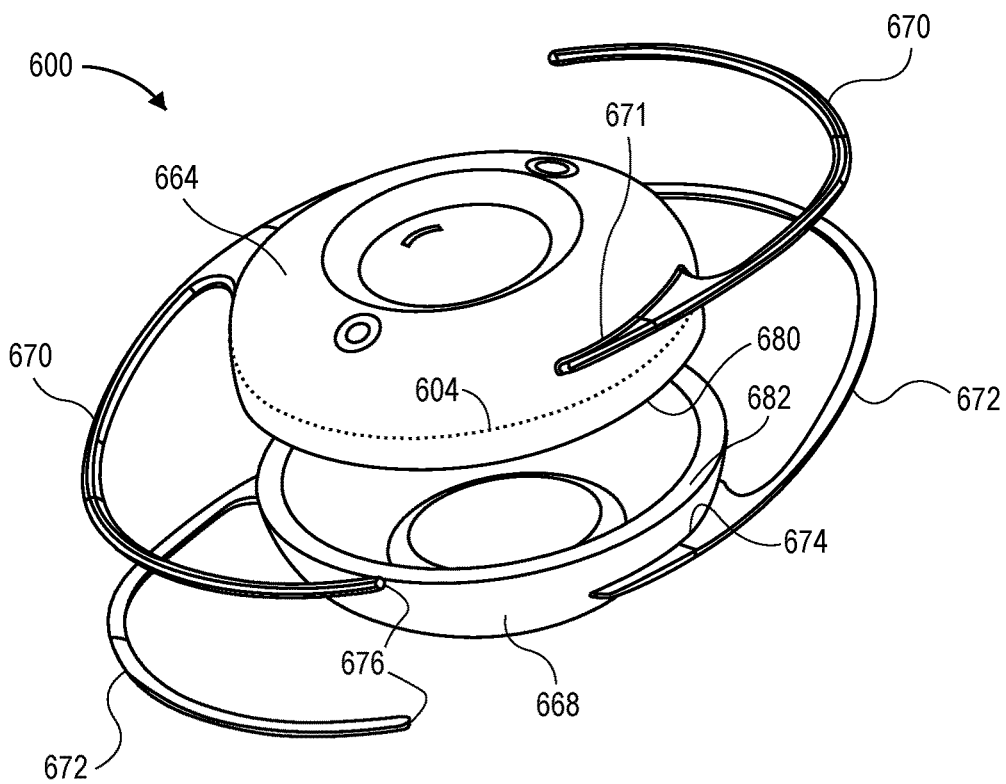
FIG. 6A is a perspective exploded view of two halves of an intraocular lens device, the anterior and posterior capsules, with haptic arms that flank the equator in accordance with an embodiment.
Figure 6B:
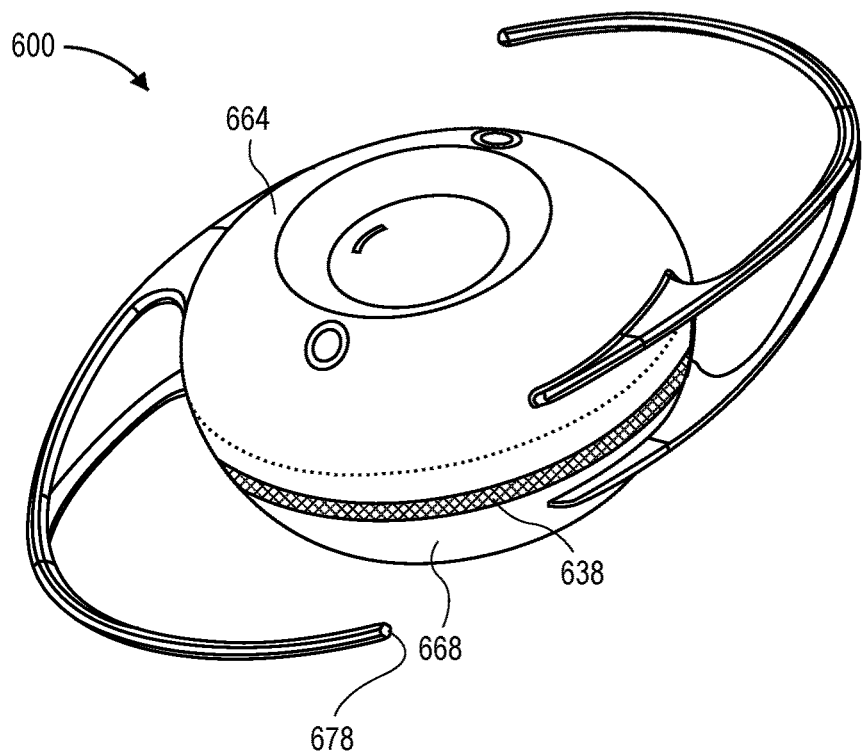
FIG. 6B is a perspective view of the two joined halves of the device of FIG. 6A.

FIGS. 6A-6B are perspective views of device 600 with haptics 670 and 672 stemming from anterior half 664 and posterior half 668, respectively. As with haptics in other ocular devices, the haptics support the device in the subject's lens capsule that is associated with the action of the ciliary muscle, adjusting the shape of the capsule. The haptics can also be sutured directly into the eye wall where the ciliary body is and can be used either where there is no capsular bag or a compromised capsular bag. Haptics can be made of polyvinylidene fluoride (PVDF), polymethyl methacrylate (PMMA), polyimide, acrylate, or other resilient biocompatible materials.

FIG. 6A illustrates halves prior to joining, with anterior portion 664 having the largest width circumference, equator 604. Mouth 680 of the sack of anterior half 664 has a smaller diameter than equator 604. At point 671 on anterior portion 664, haptic anterior connecting arm 670 is connected to its outer surface. The point is about halfway between the seam and a pole of hemispherical half 664, i.e., at one half the thickness of anterior half 664. A second connecting arm 670, of the same set of haptic arms, is disposed on an opposite side on the same hemisphere.

Similarly, on posterior half 668 haptic anterior connecting arm 672 is connected at point 674 to the posterior half's outer surface. Point 674 is about halfway between the seam and a pole of hemispherical half 668, i.e., at one half the thickness of posterior half 668. A second connecting arm 672, of the second set of haptic arms on posterior half 668, is disposed on an opposite side on the same hemisphere.

At this point, ends 676 of haptic arms 670 and 672 are free. When the two hemispheres, anterior half 664 and posterior half 668, are joined together, the haptic arms may remain free. Or each haptic arm may be mated to its respective arm on the opposite hemisphere.

FIG. 6A shows that rim 682 of the pliable bowl of posterior half 668 is wider than any other portion of posterior half 668. To join the halves together, rim 682 of bowl-shaped posterior hemisphere 668 is joined all of the way around and sealed with mouth 680 of anterior hemisphere 664.

FIG. 6B illustrates anterior half 664 and posterior half 668 joined together at seam area 638. In this exemplary embodiment, the ends of the haptic arms are angled and joined together to form Y-shaped structures with joined ends 678. They can be bonded with a glue, such as silicone.

A technical advantage of this configuration, with the front connecting arms joined at their ends to the rear connecting arms, is that the arms avoid seam 638 between the halves and avoid equator 604. It has been demonstrated by mechanical simulation analysis and experiments that an optimal force position can be found for the connection position of the haptics. The split Y design can facilitate the force balance of the capsule in refractive adjustment. It can also achieve controllable deformation, thereby increasing the accuracy and effectiveness of refractive adjustment.

Figure 7:
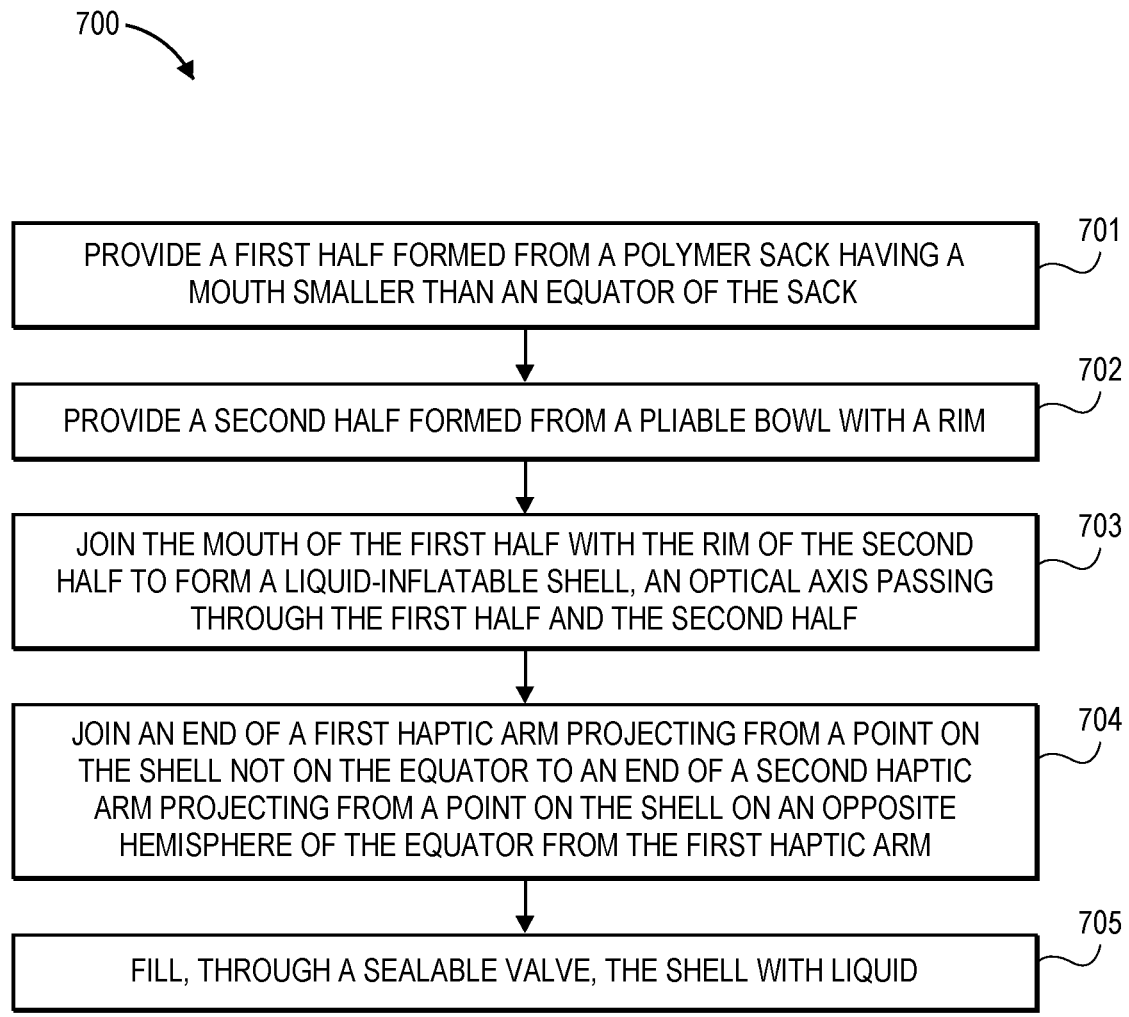
FIG. 7 is a flowchart illustrating a process in accordance with an embodiment.

FIG. 7 is a flowchart illustrating a process in accordance with an embodiment. In operation 701, a first half formed from a polymer sack having a mouth smaller than an equator of the sack is provided. In operation 702, a second half formed from a pliable bowl with a rim is provided. In operation 703, the mouth of the first half is joined with the rim of the second half to form a liquid-inflatable shell, an optical axis passing through the first half and the second half. In operation 704, an end of a first haptic arm projecting from a point on the shell not on the equator is joined to an end of a second haptic arm projecting from a point on the shell on an opposite hemisphere of the equator from the first haptic arm. In operation 705, the shell is filled with liquid through a sealable valve.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" in reference to a temperature or other engineering units includes measurements or settings that are within +1%, +2%, +5%, +10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. An accommodating intraocular lens apparatus comprising:
   a first half formed from a polymer sack having a mouth smaller than an equator of the sack;
   a second half formed from a pliable bowl with a rim;

a seam joining the mouth of the first half with the rim of the second half to form a liquid-inflatable shell, an optical axis passing through the first half and the second half;

a sealable valve in the shell;

a haptic arm projecting from the first half; and a haptic arm projecting from the second half, wherein the haptic arms are joined at ends that are away from the shell and equator.

2. The apparatus of claim 1 wherein the seam is parallel to the equator.

3. The apparatus of claim 2 wherein a distance between the seam and the equator is between 1.0 millimeter and 1.5 millimeters.

4. The apparatus of claim 1 further comprising:

a depression formed in the shell, the depression having a continuous rim disposed around the optical axis, the continuous rim configured to seal against an enveloping capsular bag when implanted.

5. The apparatus of claim 4 wherein a highest point within the depression is lower than the continuous rim when the shell is full of liquid, the depression being configured to hold an enveloping capsular bag away from shell wall material within the depression.

6. The apparatus of claim 4 further comprising:

a second depression formed in the shell, the second depression having a continuous rim disposed around the optical axis, the continuous rim of the second depression configured to seal against an enveloping capsular bag when implanted.

7. The apparatus of claim 6 wherein a highest point within the second depression is lower than the continuous rim of the second depression when the shell is full of liquid, the second depression being configured to hold an enveloping capsular bag away from shell wall material within the second depression.

8. The apparatus of claim 1 wherein the haptic arm projecting from the first half is connected to the equator.

9. The apparatus of claim 1 wherein the haptic arm projecting from the first half does not project from the equator.

10. The apparatus of claim 9 wherein the haptic arms flank the equator.

11. The apparatus of claim 1 wherein the joined ends of the haptic arms and angles between the haptic arms form a Y-shaped structure.

12. The apparatus of claim 1 wherein the haptic arm projecting from the first half is connected to the first half at one-half a thickness of the first half, and the haptic arm projecting from the second half is connected to the second half at one-half a thickness of the second half.

13. The apparatus of claim 1 wherein the sealable valve includes:

an annulus; and a self-sealing polymer body surrounded by the annulus, the polymer body being softer than the annulus.

14. The apparatus of claim 13 wherein a hardness of the annulus is between 80A Shore and 90A Shore, and a hardness of the polymer body is between 20A Shore and 40A Shore.

15. The apparatus of claim 1 further comprising:

a layer of parylene over an outer surface of the sealable valve.

16. The apparatus of claim 1 further comprising:

liquid filling the liquid-inflatable shell.

17. A method of manufacturing and testing an accommodating intraocular lens, the method comprising:

providing a first half formed from a polymer sack having a mouth smaller than an equator of the sack;

providing a second half formed from a pliable bowl with a rim;

joining the mouth of the first half with the rim of the second half to form a liquid-inflatable shell, an optical axis passing through the first half and the second half;

mating an end of a first haptic arm projecting from the first half to an end of a second 8 haptic arm projecting from the second half, wherein the joined ends are away from the shell and the equator; and filling, through a sealable valve, the shell with liquid.

18. The method of claim 17 wherein the joining includes adding uncured polymer across the first and second halves to form a seam, wherein the seam is parallel to the equator.

19. The method of claim 17 further comprising:

squeezing the equator to increase a wall curvature of the one of the halves around the optical axis more than a wall curvature of the other half around the optical axis.

20. The method of claim 17 wherein the haptic arm projecting from the first half does not project from the equator.

* * * * *

UNITED STATES PATENT AND TRADEMARK OFFICE
CERTIFICATE OF CORRECTION

PATENT NO. : 12,295,831 B2
APPLICATION NO. : 18/508702
DATED : May 13, 2025
INVENTOR(S) : Yu-Chong Tai and Mark S. Humayun Page 1 of 1

It is certified that error appears in the above-identified patent and that said Letters Patent is hereby corrected as shown below:

In the Claims

Column 10, Line 32 (Claim 17 Line 11) delete "second 8 haptic" and insert --second haptic--.

Signed and Sealed this
Twenty-fourth Day of June, 2025

Coke Morgan Stewart
*Acting Director of the United States Patent and Trademark Office*